(12) United States Patent
Mazar et al.

(10) Patent No.: US 6,896,870 B1
(45) Date of Patent: May 24, 2005

(54) DIAGNOSTIC PROBES AND THERAPEUTICS TARGETING UPA AND UPAR

(75) Inventors: Andrew P. Mazar, La Jolla, CA (US); Terence R. Jones, San Diego, CA (US)

(73) Assignee: Angstrom Pharmaceuticals, Inc., San Diego, CA (US)

( * ) Notice: Subject to any disclaimer, the term of this patent is extended or adjusted under 35 U.S.C. 154(b) by 447 days.

(21) Appl. No.: 09/670,537

(22) Filed: Sep. 27, 2000

Related U.S. Application Data

(60) Provisional application No. 60/157,012, filed on Oct. 1, 1999.

(51) Int. Cl.$^7$ .................. A61K 51/00; A61M 36/14
(52) U.S. Cl. .................. 424/1.69; 424/9.1; 424/1.11; 514/2
(58) Field of Search .................. 424/1.11, 1.65, 424/1.69, 9.1, 9.2, 9.3, 9.4, 9.5, 9.6; 514/2; 534/10–16; 530/300

(56) References Cited

FOREIGN PATENT DOCUMENTS

| | | |
|---|---|---|
| EP | 0 890 638 | 1/1999 |
| WO | WO 90/12091 | 10/1990 |
| WO | WO 98/21230 | 5/1998 |
| WO | WO 99/48509 | 9/1999 |

OTHER PUBLICATIONS

Higgins et al, 1986, Archives of Biochemistry and Biophysics, Vo. 249, No. 2, pp. 418–426.*

Ettore Appella et al., "The Receptor–binding Sequence of Urokinase", The Journal of Biological Chemistry, vol. 262, No. 10, Apr. 6, 1987, pp. 4437–4440.

Michael Ploug et al., "Photoaffinity Labeling of the Human Receptor for Urokinase–Type Plasminofen Activator Using a Decapeptide Anatgonist. Evidence for a Composite Ligand–Binding site and a Short Interdomain Separation", Biochemistry, 1998, 37, 3612–3622.

* cited by examiner

*Primary Examiner*—Dameron L. Jones
(74) *Attorney, Agent, or Firm*—McDermott Will & Emery LLP

(57) ABSTRACT

A uPAR-targeting protein or peptide is diagnostically or therapeutically labeled and used in methods of diagnosis of therapy. The labeled protein or peptide preferably has the following properties: it comprises at least 38 amino acid residues, including residues 13–30 of the uPAR-binding site of uPA; competes with labeled DFP-uPA for binding to a cell or molecule that has a binding site for uPA, and has an $IC_{50}$ value of about 10 nM or less; and is not a fusion protein wherein the uPA peptide is fused to another non-uPA protein or peptide. Preferred molecules are uPA, scuPA, tcuPA, an N-terminal fragment of uPA, residues 1–135, an N-terminal fragment of uPA, residues 1–143, an N-terminal fragment of uPA, residues 1–43; or an N-terminal fragment of uPA, residues 4–43. Detectable labels include a radionuclide, a PET-imageable agent, an MRI-imageable agent, a fluorescer, a fluorogen, a chromophore, a chromogen, a phosphorescer, a chemiluminescer or a bioluminescer. The disclosed methods are used to inhibit cell migration, cell invasion, cell proliferation or angiogenesis, or to induce apoptosis, preferably in the treatment of a subject having a disease or condition associated with undesired cell migration, invasion, proliferation or angiogenesis.

19 Claims, 1 Drawing Sheet

Urokinase Plasminogen Activator (uPA)

DIAGNOSTIC PROBES AND THERAPEUTICS TARGETING UPA AND UPAR

This application is based on, and claims the benefit of, U.S. Provisional Application No. 60/157,012, filed Oct. 1, 1999, which is incorporated herein by reference.

BACKGROUND OF THE INVENTION

1. Field of the Invention

The present invention relates to conjugates of the urokinase plasminogen activator (uPA) and its fragments that bind to the cell surface receptor uPA (uPAR), the peptides and constructs labeled to deliver a diagnostic probe or a therapeutic agent to the surfaces of cells expressing uPAR. The proteins and peptides of the invention are capable of carrying a suitable detectable or imageable label that will allow qualitative detection and also quantitation of uPAR levels in vitro and in vivo. Such labeled peptide compositions are therefore useful as diagnostic, prognostic and imaging tools in all diseases and conditions where this receptor plays a pathological or otherwise undesirable role. cDNA probes that detect uPA and uPAR-expressing cells may also be conjugated with similar diagnostic labels and used in in situ hybridization assays. Furthermore, by targeting therapeutic agents that "label" the peptide to uPAR, it is possible to achieve a number of biological effects that include cell death, the inhibition of cell movement and migration and the inhibition of angiogenesis.

2. Description of the Background Art

Urokinase-type plasminogen activator (uPA) has been identified as the initiator of several cascades related to tumor progression, invasion and angiogenesis. The uPA system is strongly linked to pathological processes, such as cell invasion and metastasis in cancer (Danø et al., *Adv. Cancer Res.*, 44:139–266 (1985)).

Cells produce uPA in an inactive form as a 411 amino acid protein, pro-urokinase (pro-uPA) or single-chain uPA (scuPA), which then binds to its receptor, uPAR. This binding event is a prerequisite for the efficient activation of scuPA to two-chain uPA (tcuPA) in a cellular milieu (Ellis et al., *J. Biol. Chem.*, 264:2185–88 (1989)). Pro-uPA is activated by a single proteolytic cleavage between amino acid 158 (Lys) and 159 (Ile) to activate the proenzyme. Cleavage results in the formation of the two-chain active uPA (tcuPA). Cleavage of pro-uPA at the activation site in fact results in a conformational change and in the gain of plasminogen activator activity both with natural and synthetic substrates.

uPA is a three-domain protein comprising (1) an N-terminal "growth factor domain" (GFD), (2) a kringle domain, and (3) a C-terminal serine protease domain. uPAR, the receptor for pro-uPA, is also a multi-domain protein anchored by a glycosylphosphatidyl-inositol anchor to the outer leaf of the cell membrane (Behrendt et al., *Biol. Chem. Hoppe-Seyler*, 376:269–279 (1995)).

The amino acid sequence of the N-terminus of human pro-uPA (residues 1–44, SEQ ID NO:1) is The structure of pro-uPA is shown in FIG. 1.

Therapeutic use of uPA, pro-uPA, tissue plasminogen activator (tPA) or streptokinase (for thromboembolism) requires very high dosage due in part to their very rapid clearance. Possible reasons for the short half-life include binding to specific circulating inhibitors, binding to receptors, internalization and degradation of inhibitor-bound and/or receptor-bound PA.

uPAR is not normally expressed at detectable levels on quiescent cells and must therefore be upregulated before it can initiate the activities of the uPA system. uPAR expression is stimulated in vitro by differentiating agents such as phorbol esters (Lund et al., *J. Biol. Chem.* 266:5177–5181 (1991)), by the transformation of epithelial cells, and by various growth factors and cytokines such as VEGF, bFGF, HGF, IL-1, TNFα in endothelial cells and by GM-CSF in macrophages (Mignatti et al., *J. Cell Biol.* 113:1193–1201 (1991); Mandriota et al., *J. Biol. Chem.* 270:9709–9716; Yoshida et al., *Inflammation* 20:319–326 (1996)). This upregulation has the functional consequence of increasing cell motility, invasion, and adhesion (Mandriota et al., supra). More importantly, uPAR appears to be up-regulated in vivo in most human carcinomas examined to date, specifically, in the tumor cells themselves, in tumor-associated endothelial cells undergoing angiogenesis and in macrophages (Pyke et al., *Cancer Res.* 53:1911–15 (1993) which may participate in the induction of tumor angiogenesis (Lewis et al., *J. Leukoc. Biol.* 57:747–751 (1995)). uPAR expression in cancer patients is present in advanced disease and has been correlated with a poor prognosis in numerous human carcinomas (Hofmann et al., *Cancer* 78:487–92 (1996); Heiss et al., *Nature Med.* 1:1035–39 (1995). Moreover, uPAR is not expressed uniformly throughout a tumor but tends to be associated with the invasive margin and is considered to represent a phenotypic marker of metastasis in human gastric cancer. The fact that uPAR expression is up-regulated only in pathological states involving extracellular matrix remodeling and cell motility such as cancer makes it an attractive marker for diagnosis as well as a selective target for therapy.

Earlier studies with peptide fragments within the GFD of uPA had shown that residues 20–30 conferred the specificity of binding, but that residues 13–19 were also needed if residues 20–30 were to attain the proper binding conformation. Specifically, the peptide [Ala$^{19}$]uPA(12–32), which contains two cysteines (the third cysteine being replaced by Ala to avoid undesired disulfide bond formations) in its open chain form prevented uPA binding to uPAR with an IC$_{50}$ of 100 nM. In its oxidized cyclic form with an intrachain disulfide bond between Cys$^{13}$ and Cys$^{31}$, the peptide prevented uPA binding with an IC$_{50}$ of 40 nM. The authors proposed that residues 13–19 might act indirectly to provide a scaffold that would help residues 20–30 attain the correct binding conformation (Appella et al., *J. Biol. Chem.*, 262:4437–4440 (1987).

A related commonly-assigned patent (U.S. Pat. No. 5,942,492) and application (U.S. Ser. No. 09/1,816), both of which

```
Ser Asn Glu Leu His Gln Val Pro Ser Asn Cys Asp Cys Leu Asn Gly
1                                   10

Gly Thr Cys Val Ser Asn Lys Tyr Phe Ser Asn Ile His Trp Cys Asn
              20                                  30

Cys Pro Lys Lys Phe Gly Gly Gln His Cys Glu Ile
                    40
``` are incorporated herein by reference in their entirety, show that novel cyclic molecules derived from the uPA peptide fragment 20–30 (in which residue 20 is covalently bonded to residue 30) bind to uPAR with $IC_{50}$ values in the 10–100 nM range.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have discovered that relatively large uPA peptides that are cleared rapidly from the body are useful as diagnostic agents (as well as in therapy). These include, but are not limited to, high molecular weight uPA (residues 1–411); single-chain uPA (scuPA) described above; tcuPA, DFP-uPA (tcuPA inactivated with the suicide inhibitor diisopropyl fluorophosphate), the N-terminal fragment often designated ATF, which is a peptide of 135 or 143 amino acids having the sequence of 1–135 or 1–143 of native uPA; the GFD which corresponds to residues 4–43.

The preferred uPAR-targeting protein or peptide has the following characteristics:
(a) diagnostically or therapeutically labeled (which terms are defined below);
(b) comprises at least 38 amino acid residues;
(c) includes residues 13–30 of the uPAR-binding site of uPA.
(d) competes with labeled DFP-uPA (preferably [$^{125}$I] labeled) for binding to a cell or molecule that has a binding site for uPA, and has an $IC_{50}$ value of about 10 nM or less—that is, the protein or peptide causes 50% inhibition of the binding of the labeled ligand at concentrations of 10 nM or lower).
(e) is not a fusion protein wherein the uPA peptide is fused to another (non-uPA) protein or peptide.

Preferred detectable labels include a radionuclides, PET-imageable agents, MRI-imageable agents, fluorescers, fluorogens, a chromophore, a chromogen, a phosphorescer, a chemiluminescer or a bioluminescer. Such a label permits detection or quantitation of the uPAR level in a tissue sample and can be used, therefore, as a diagnostic and a prognostic tool in all diseases where enhanced expression of the receptor plays a pathological or otherwise undesirable role, including those described herein.

A most preferred radionuclide is selected from the group consisting of $^3$H, $^{14}$C, $^{35}$S, $^{99}$Tc, $^{123}$I, $^{125}$I, $^{131}$I, $^{111}$In, $^{97}$Ru, $^{67}$Ga, $^{68}$Ga, $^{72}$As, $^{89}$Zr and $^{201}$Tl. In the diagnostic composition, the fluorescer or fluorogen is preferably fluorescein, rhodamine, dansyl, phycoerythrin, phycocyanin, allophycocyanin, o-phthaldehyde, fluorescamine, a fluorescein derivative, Oregon Green, Rhodamine Green, Rhodol Green or Texas Red.

A protein or peptide probe of this invention, e.g., labeled tcuPA, has the advantage that it may be internalized by the cells to which it binds, e.g., tumor cells. This property is useful for imaging techniques in which it is especially important to reduce background signal (the circulating or non-specifically bound probe molecules) relative to specifically bound probe. This uptake permits clearance of circulating probe so that the ratio of labeled probe inside tumor cells to the probe elsewhere in the body increases. Shorter peptides, such as those described in the Background section, would not be expected to behave in this way. Thus, the present invention provides agents with increased "contrast" for detecting tumors or other sites of cells that express uPAR.

The present invention provides the first specifically-targeted contrast agent for magnetic resonance imaging (MRI). The specificity is a result of the enhanced expression of uPAR in the target tissue, generally tumor tissue. Some of the peptides that bind uPAR and, as a result undergo activation, may be quenched by the naturally occurring plasminogen activator inhibitor-1 (PAI-1) and are taken up by a uPAR-dependent mechanism as uPA peptide-PAI-1 complexes.

Preferably, a diagnostic label is bound to the protein or peptide through one or more diethylenetriaminepentaacetic acid (DTPA) residues that are coupled to the protein or peptide. In a preferred embodiment, where labeling is targeted, the label is bound through one DTPA residue. A most preferred diagnostic peptides is scuPA or ATF 1–135 coupled to one (or more) DTPA residues, to which are bound gadolinium atoms. Preferred diagnostic methods comprise MRI using these labeled peptides.

In another embodiment, the protein or peptide carries a suitable therapeutic "label" also referred to herein as a "therapeutic moiety." A therapeutic moiety is an atom, a molecule, a compound or any chemical component added to the peptide that renders it active in treating a disease or condition associated with enhanced expression of uPAR. The peptides of the present invention are prepared by conventional means, either recombinant or by proteolysis of uPA as described in Mazar et as., (*Fibrinolysis* 6 (*suppl.* 1): 49–55), hereby incorporated by reference in its entirety. The therapeutically active moiety may be bound directly or indirectly to the peptide. The therapeutic composition may be one in which the therapeutic moiety is bound to the active site of the uPA protein or peptide; such compositions are made from compounds described below. The therapeutically labeled protein or peptide is administered as pharmaceutical composition which comprises a pharmaceutically acceptable carrier or excipient, and is preferably in a form suitable for injection.

In the above pharmaceutical composition, the therapeutically active moiety is preferably a radionuclide. Examples of radionuclides include $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb and $^{217}$Bi.

The present invention also provides a uPA active site-targeting compound that covalently modifies the active site of tcuPA or a fragment or subunit thereof, which fragment or subunit retains (i) the uPA enzymatic endosite and (ii) a uPAR-binding epitope. This compound may include (a) a detectable label; (b) a therapeutic moiety; or (c) a chelator that is optionally bound to a detectable label or a therapeutic moiety. The compound localizes said chelator, detectable label or therapeutic moiety to the uPA active site.

The above compound may be an affinity label or a uPA-activated irreversible inhibitor. Preferred affinity labels are alkylating groups, such as chloromethylketone (CMK).

The above compound preferably has a structure characterized by one of the following four general formulas, (wherein $(Xaa)_{2-6}$-(Lys,Arg) is SEQ ID NO:2 throughout the specification):

(Label)-$(Xaa)_{2-6}$-(Lys,Arg)-(alkylating group);

(Therapeutic moiety)-$(Xaa)_{2-6}$-(Lys,Arg)-(alkylating group);

$(Chelator_{(empty)})$-$(Xaa)_{2-6}$-(Lys,Arg)-(alkylating group); or (Label-Chelator)-$(Xaa)_{2-6}$-(Lys,Arg)-(alkylating group), where Xaa is any amino acid and the "label" is a detectable label. In these formulas and throughout the specification, the expression (Lys,Arg) means a single amino acid that is either Lys or Arg. Preferably (Xaa)$_{2-6}$ is Glu-Gly, resulting in compounds of the formula:

(Chelator$_{(empty)}$)-Glu-Gly-Arg-CMK; or (Label-Chelator)-Glu-Gly-Arg-CMK.

Also provided is a molecule, comprising uPA, tcuPA or a fragment or subunit thereof, which fragment or subunit retains (i) the uPA enzymatic endosite and (ii) a uPAR-binding epitope, and which uPA, tcuPA, fragment or subunit is bonded covalently to the compound described above. This molecule would have the general formula:

(Chelator$_{(empty)}$)-(Xaa)$_{2-6}$-(Lys,Arg)-(alkylating group)-uPA; or (Label-Chelator)-(Xaa)$_{2-6}$-(Lys,Arg)-(alkylating group)-uPA.

Another embodiment of a uPA active site-targeting peptide compound is one that binds to the endosite and one or more exosites of tcuPA or of a tcuPA fragment or subunit (which fragment or subunit retains the uPA (i) enzymatic endosite and (ii) a uPAR-binding epitope). The peptide compound, which covalently modifies the endosite, preferably includes either (a) detectable label, (b) a therapeutic moiety, or (c) a chelator that is optionally bound to a detectable label or to a therapeutic moiety. This peptide compound localizes said chelator, detectable label or therapeutic moiety to the uPA active site.

The above peptide compound of claim preferably has a structure defined by one of the following four general formulas (Label)-(Peptide Z)-(Xaa)$_{2-6}$-(Lys,Arg)-(alkylating group);

(Therapeutic Moiety)-(Peptide Z)-(Xaa)$_{2-6}$-(Lys,Arg)-(alkylating group), (Chelator$_{(empty)}$)-(Peptide Z)-(Xaa)$_{2-6}$-(Lys,Arg)-(alkylating group); or (Label-Chelator)-(Peptide Z)-(Xaa)$_{2-6}$-(Lys,Arg)-(alkylating group).

The (Label) is a detectable label, Xaa is any amino acid and Peptide Z is any peptide that binds to a surface exosite of uPA.

Also included is a molecule, comprising uPA, tcuPA or a fragment or subunit of tcuPA bonded at the uPA endosite and at one or more exosites to the above peptide compound.

In the above method, the protein or peptide is preferably scuPA or said N-terminal fragment of uPA residues 1–135 and the detectable label is preferably gadolinium.

The invention includes methods of using the above classes of molecules, specifically, in a method for detecting the presence of uPAR (i) on the surface of a cell, (ii) in a tissue, (iii) in an organ or (iv) in a biological sample, which cell, tissue, organ or sample is suspected of expressing uPAR due to a pathological state. The method comprising the steps of (a) contacting the cell, tissue, organ or sample with any of the diagnostic and detectably labeled compositions and molecules described above; and (b) detecting the presence of the label associated with the cell, tissue, organ or sample. In this method, both the contacting and the detecting may be conducted in vitro. Alternatively, the contacting is in vivo and the detecting is in vitro. Preferably, the contacting and the detecting are in vivo.

A nonlimiting group of diseases or conditions treatable by therapeutically labeled peptides of this invention include primary growth of solid tumors or leukemias and lymphomas, metastasis, invasion and/or growth of tumor metastases.

The present invention also provides a method for inhibiting cell migration, cell invasion, cell proliferation or angiogenesis, or for inducing apoptosis, comprising contacting cells associated with undesired cell migration, invasion, proliferation or angiogenesis with an effective amount of the above therapeutically labeled composition. Preferably, the method is used to inhibit the invasiveness of tumor cells.

Diseases or conditions treatable by the present composition include primary growth of a solid tumor, leukemia or lymphoma; tumor invasion, metastasis or growth of tumor metastases; benign hyperplasia; atherosclerosis; myocardial angiogenesis; post-balloon angioplasty vascular restenosis; neointima formation following vascular trauma; vascular graft restenosis; coronary collateral formation; deep venous thrombosis; ischemic limb angiogenesis; telangiectasia; pyogenic granuloma; corneal disease; rubeosis; neovascular glaucoma; diabetic and other retinopathy; retrolental fibroplasia; diabetic neovascularization; macular degeneration; endometriosis; arthritis; fibrosis associated with a chronic inflammatory condition, traumatic spinal cord injury including ischemia, scarring or fibrosis; lung fibrosis, chemotherapy-induced fibrosis; wound healing with scarring and fibrosis; peptic ulcers; a bone fracture; keloids; or a disorder of vasculogenesis, hematopoiesis, ovulation, menstruation, pregnancy or placentation associated with pathogenic cell invasion or with angiogenesis.

Another preferred use of the present methods is the hybridization of a fluorescently labeled cDNA probe (FISH probe) complementary to uPA or to uPAR mRNA expressed in a tumor and detected in vitro in a paraffin embedded or frozen tissue section derived from that tumor.

DESCRIPTION OF THE PREFERRED EMBODIMENTS

Figure 1:
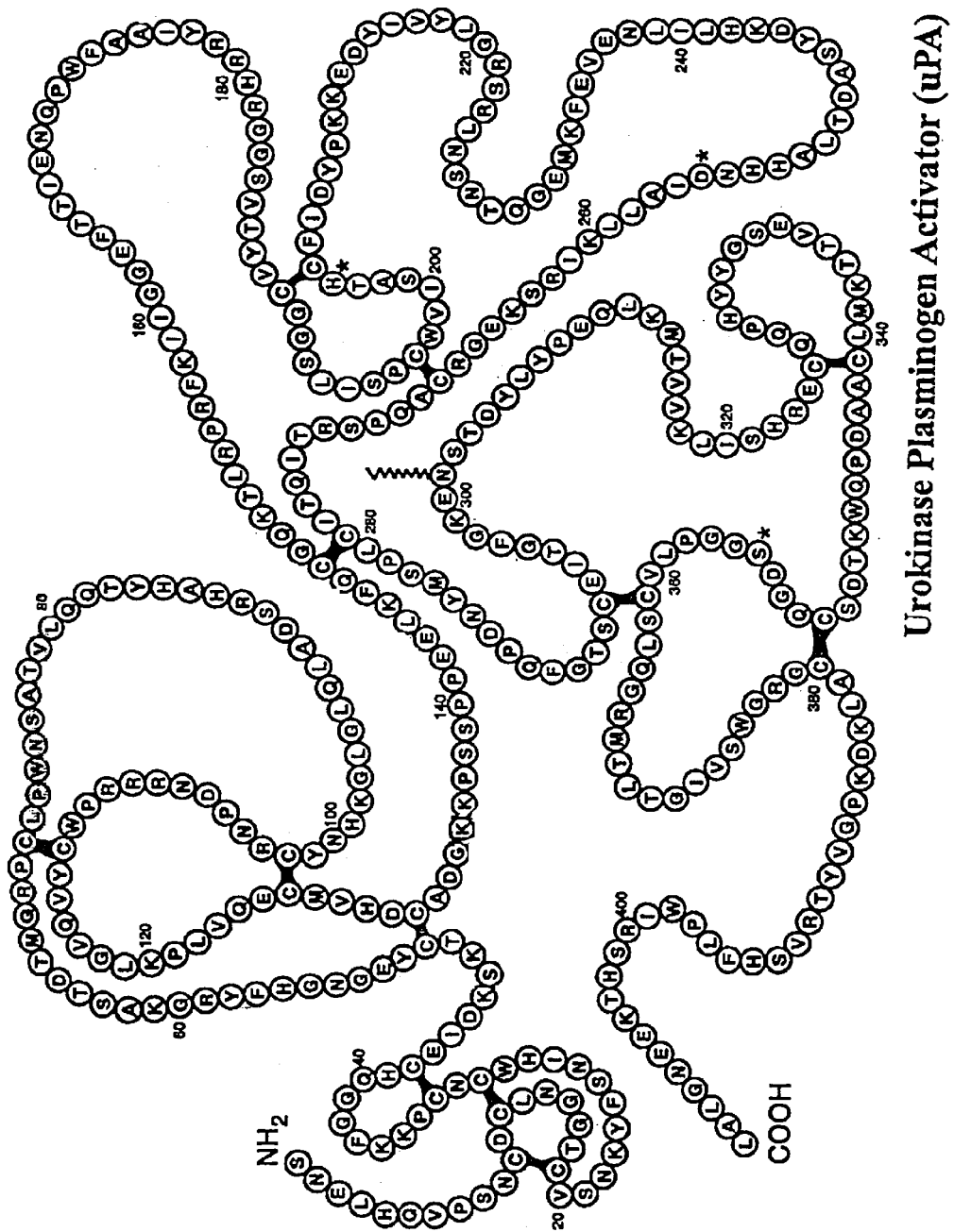
FIG. 1 is a schematic representation of the pro-uPA molecule. The N-terminal growth factor domain (ATF) of human uPA is residues 1–135.

The present inventors have discovered that relatively large uPA fragments or peptides that are capable of binding to uPAR, a receptor expressed in pathological conditions such as tumors, can be modified to incorporate diagnostic or therapeutic labels without significant alteration in their binding properties.

uPA-uPAR interactions may exhibit varying degrees of species specificity. Thus, it is always preferred to use a peptide having the amino acid sequence (or a substitution variant thereof) of the species of the animal being targeted.

In Vitro Testing of Compositions

A. Assay for Ligand Binding to uPAR on Whole Cells

The uPAR-targeting peptide compounds of the invention are readily tested for their binding to uPAR, preferably by measuring their ability to inhibit the binding of [$^{125}$I]DFP-uPA to uPAR in a competitive ligand-binding assay. The assay may employ whole cells that express uPAR, for example cell lines such as RKO or HeLa. A preferred assay is conducted as follows. Cells (about $5\times10^4$/well) are plated in medium (e.g., MEM with Earle's salts/10% FBS+ antibiotics) in 24-well plates, then incubated in a humid 5% $CO_2$ atmosphere until the cells reach 70% confluence. Catalytically inactivated high molecular weight uPA (DFP-uPA) is radioiodinated using Iodo-gen® (Pierce) to a specific activity of about 250,000 cpm/mg. The cell-containing plates are then chilled on ice and the cells are washed twice (5 minutes each) with cold PBS/0.05% Tween-80. Test compounds are serially diluted in cold PBS/0.1% BSA/0.01% Tween-80 and added to each well to a final volume of 0.3 mL 10 minutes prior to the addition of the [$^{125}$I]DFP-uPA. Each well then receives 9500 cpm of [$^{125}$I]DFP-uPA at a final concentration of 0.2 nM). The plates are then incubated at 4° C. for 2 hrs, after which time the cells are washed 3× (5 minutes each) with cold PBS/0.05% Tween-80. NaOH (1N) is added to each well in 0.5 mL to lyse the cells, and the plate is incubated for 5 minutes at room temperature or until all the cells in each well are lysed as determined by microscopic examination. The contents of each well are then aspirated and the total counts in each well determined using a gamma counter. Each compound is tested in triplicate and the results are expressed as a percentage of the total radioactivity measured in wells containing [$^{125}$I]DFP-uPA alone, which is taken to represent maximum (100%) binding.

The inhibition of binding of [$^{125}$I]DFP-uPA to uPAR is usually dose-related, such that the concentration of the test compound necessary to produce a 50% inhibition of binding (the $IC_{50}$ value), which is expected to fall in the linear part of the curve, is easily determined. In general, the compounds of the invention have $IC_{50}$ values of less than about $10^{-7}$ M. Preferably, the compounds of the invention have $IC_{50}$ values of less than about $10^{-8}$ M and, even more preferably, less than about $10^{-9}$ M.

In Vivo Study of the uPAR-Targeted Peptides

A. Xenograft Model of Subcutaneous (s.c.) Tumor Growth

Nude mice are inoculated with MDA-MB-231 cells (human breast carcinoma) and Matrigel® (1×10$^6$ cells in 0.2 mL) s.c. in the right flank of the animals. The tumors are staged to 100 mm$^3$ and then imaging with a test composition is initiated (50 μg/animal i.p.). Animals are subjected to the appropriate scanning or imaging method when tumors are expected to be at a range of volumes.

B. Xenograft Model of Metastasis

The compounds of this invention can also diagnose the presence of late metastasis using an experimental metastasis model (Crowley, C. W. et al., *Proc. Natl. Acad. Sci. USA* 90 5021–5025 (1993)). Late metastasis involves the steps of attachment and extravasation of tumor cells, local invasion, seeding, proliferation and angiogenesis. Human prostatic carcinoma cells (PC-3) are inoculated into nude mice i.v. via the tail vein and metastases identified after about 14 days, particularly in the lungs but also in regional lymph nodes, femurs and brain. This mimics the organ tropism of naturally occurring metastases in human prostate cancer. A compound of the invention (50 μg/mL) is given i.v. on day 14 and the microscopic metastases are imaged using the appropriate detection method. Tissues may also be harvested from these mice after euthanasia followed by the detection of cells expressing uPA and uPAR using the cDNA probes.

For a compound to be useful in accordance with this invention, it should demonstrate an ability to detect the presence of a tumor mass (primary or metastatic) as small as about 5 mm in a mouse model.

Diagnostic and Prognostic Compositions

The uPA peptides can be detectably labeled and used, for example, to detect a peptide binding site or receptor (such as uPAR) on the surface or in the interior of a cell. The fate of the peptide during and after binding can be followed in vitro or in vivo by using the appropriate method to detect the label. The labeled peptide may be utilized in vivo for diagnosis and prognosis, for example to image occult metastatic foci or for other types of in situ evaluations.

A number of U.S. patents, incorporated by reference herein, disclose methods and compositions for complexing metals to larger molecules, including description of useful chelating agents. The metals are preferably detectable metal atoms, including radionuclides, and are complexed to proteins and other molecules. These documents include: U.S. Pat. No. 5,627,286 (Heteroatom-bearing ligands and metal complexes thereof); U.S. Pat. No. 5,618,513 (Method for preparing radiolabeled peptides); U.S. Pat. No. 5,567,408 (YIGSR peptide radiopharmaceutical applications); U.S. Pat. No. 5,443,816 (Peptide-metal ion pharmaceutical preparation and method); U.S. Pat. No. 5,561,220 (Technetium-$^{99m}$ labeled peptides for imaging inflammation).

Suitable detectable labels include radioactive, fluorescent, fluorogenic, chromogenic, or other chemical labels. Useful radiolabels, which are detected simply by gamma counter, scintillation counter or autoradiography include $^3$H, $^{125}$I, $^{131}$I, $^{35}$S and $^{14}$C. In addition, $^{131}$I is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, *Handbook of Fluorescent Probes and Research Chemicals*, Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red™ derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., *Science* 281:2013–2016 (1998), and quantum dots, e.g., zinc-sulfide-capped cadmium selenide (Chan, W. C. W. et al., Science 281:2016–2018 (1998)).

In yet another approach, the amino group of a uPA peptide is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The peptides can also be labeled for detection using fluorescence-emitting metals such as $^{152}$Eu, or others of the lanthanide series. These metals can be attached to the peptide using such metal chelating groups as diethylenetriaminepentaacetic acid (DTPA) or ethylenediaminetetraacetic acid (EDTA). DTPA, for example, is available as the anhydride, which can readily modify the NH$_2$-containing uPAR-binding peptides of this invention.

For in vivo diagnosis, radionuclides may be bound to the peptide either directly or indirectly using a chelating agent such as DTPA and EDTA which is chemically conjugated, coupled or bound (which terms are used interchangeably) to the peptide. The chemistry of chelation is well known in the art, and a varying range of molar ratios of DTPA: peptide may be used to produce the DTPA-coupled peptide, and thereby, the diagnostically labeled peptide. The key limiting factor on the chemistry of coupling is that the uPA fragment must maintain its ability to bind uPAR after labeling. The term "chelating agent" and "chelator" and "chelating group" are meant to be synonymous and to be distinct from "chelate" which is the formed complex comprising the chelator and the metal atom or ion.

Any radionuclide having diagnostic or therapeutic value can be used as the radiolabel in the present invention. In a preferred embodiment, the radionuclide is a γ-emitting or beta-emitting radionuclide, for example, one selected from the lanthanide or actinide series of the elements. Positron-emitting radionuclides, e.g. $^{68}$Ga or $^{64}$Cu, may also be used. Suitable gamma-emitting radionuclides include those which are useful in diagnostic imaging applications. The gamma-emitting radionuclides preferably have a half-life of from 1 hour to 40 days, preferably from 12 hours to 3 days. Examples of suitable gamma-emitting radionuclides include $^{67}$Ga, $^{111}$In, $^{99m}$Tc, $^{169}$Yb and $^{186}$Re. Most preferably, the radionuclide is $^{99m}$Tc.

Examples of preferred radionuclides (ordered by atomic number) are $^{67}$Cu, $^{67}$Ga, $^{68}$Ga, $^{72}$As, $^{89}$Zr, $^{90}$Y, $^{97}$Ru, $^{99}$Tc, $^{111}$In, $^{123}$I, $^{125}$I, $^{131}$I, $^{169}$Yb, $^{186}$Re, and $^{201}$Tl. Most preferred are gamma-emitting radionuclides such as $^{67}$Ga, $^{111}$In, $^{99m}$Tc, $^{169}$Yb and $^{186}$Re, most preferably $^{99m}$Tc. Though limited work have been done with positron-emitting radiometals as labels, certain proteins, such as transferrin and human serum albumin, have been labeled with $^{68}$Ga.

A number of metals (not radioisotopes) useful for MRI include gadolinium, manganese, copper, iron, gold and europium. Gadolinium is most preferred. Generally, the amount of labeled peptide needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The peptides can also be made detectable by coupling them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

The term "diagnostically labeled" means that the peptide has attached to it a diagnostically detectable label. There are many different labels and methods of labeling known to those of ordinary skill in the art. Examples of the types of labels which can be used in the present invention include radioactive isotopes, paramagnetic isotopes, and compounds which can be imaged by positron emission tomography (PET) and by MRI. Those of ordinary skill in the art will know of other suitable labels for binding to the peptides used in the invention, or will be able to ascertain such, by routine experimentation.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140–200 keV range, which may be readily detected by conventional gamma cameras.

In vivo imaging may be used to detect occult metastases which are not observable by other methods. The expression of uPAR correlates with progression of diseases in cancer patients such that patients with late stage cancer have higher levels of uPAR in both their primary tumors and metastases. uPAR-targeted imaging could be used to stage tumors non-invasively or to detect other diseases which are associated with the presence of increased levels of uPAR (for example, restenosis that occurs following angioplasty).

The compositions of the present invention may be used in diagnostic, prognostic or research procedures in conjunction with any appropriate cell, tissue, organ or biological sample of the desired animal species. By the term "biological sample" is intended any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is a organ or tissue extract and a culture fluid in which any cells or tissue preparation from the subject has been incubated.

The labeled peptide compounds of the invention, as well as diagnostically acceptable salts thereof, may be incorporated into convenient dosage forms.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The present invention may be used in the diagnosis of any of a number of animal genera and species, and are equally applicable in the practice of human or veterinary medicine. Thus, the compositions can be used with domestic and commercial animals, including birds and more preferably mammals, as well as humans.

The peptides in a form suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

An alternative diagnostic approach utilizes cDNA probes that are complementary to and thereby detect uPA and uPAR-expressing cells by in situ hybridization with mRNA in these cells. This cDNA is preferably fluorescently labeled. This method and the preparations useful therein are described below.

Active Site-Specific Modification of uPA and Other Serine Proteases

The present invention is directed to an active site-specific reagent that covalently modifies the active site ("endosite") of uPA or any serine protease and localizes a detectable label, preferably an imageable label, or a therapeutic moiety such as a radioisotope, toxin or drug conjugate, to the endosite. To be useful in this embodiment, the uPA must be tcuPA or a similar molecule that retains the enzymatic endosite of uPA and its uPAR-binding epitope. Such a reagent is preferably an active site-directed affinity label or an enzyme-activated irreversible inhibitor of uPA activity ("suicide substrate"). In one embodiment, the reagent is attached directly (i.e., without the mediation of a chelating agent) to a detectable label or therapeutic moiety. In another embodiment, the reagent includes as part of its structure a chelating agent, as described above, that is either loaded with the label (or therapeutic moiety) or to which the label (or therapeutic moiety) may be added after the chelator has been delivered to the enzyme's endosite. The endosite-specific reagent is preferably a modified peptide, but may also be a non-peptidic molecule, as described below.

The molecules and approaches described herein are useful for other serine proteases, which utilize a similar catalytic mechanism as uPA based on the canonical catalytic triad of Ser, His and Asp common to all serine proteases. Thus, any active site-directed affinity label or suicide substrate of any serine protease can be used to localize to the endosite of that protease a chelating agent or a chelate that includes a detectable (preferably imageable) label or therapeutic moiety.

A typical example of such a reagent is an endosite-specific affinity label comprising a tripeptide and any alkylating moiety. Upon being localized to the active site of a serine protease, the reagent reacts with the active site histidine. A preferred alkylating moiety is a halomethylketone, more preferably chloromethylketone ("CMK"). A preferred endosite-specific tripeptide for uPA is Glu-Gly-Arg. Thus a preferred reagent is Glu-Gly-Arg-CMK to which is bonded a label, a therapeutic moiety or a chelating agent optionally loaded with a label or therapeutic moiety. This reagent molecule targets the His residue within the serine protease catalytic triad of uPA and covalently bonds to this His residue. Other peptides that may be longer than a tripeptide are also useful—they may have even higher affinities or be more reactive than Glu-Gly-Arg for the protease endosite and could also access exosites, thereby resulting in increased binding affinity and specificity. Bock reported the incorporation of spectroscopic probes into active sites of certain serine proteases by inactivating the enzyme with a thioester derivative of a peptide CHK. The thiol group that is generated can serve as a unique suite for subsequent labeling with thiol-reactive probes, exemplified by 5-(iodoacetamido) fluorescein (Bock, P. E., *Biochemistry* 27:6633–6639 (1999), incorporated by reference in its entirety). Thus, the present approach may be extended along these lines for incorporating the various types of detectable labels or therapeutic moieties not contemplated by Bock for the uses set forth herein.

It is within the skill of the art to test other peptides or similar molecules for binding to the uPA endosite using conventional means, and thereby determine their suitability for use in accordance with this invention. All that is required is the peptide portion of the reagent have a basic residue (Lys or Arg) at the "S1" site. Thus for example, the peptide part of the molecule may have the following structure (where Xaa symbolizes any amino acid residue): $(Xaa)_{2-6}$-(Lys, Arg), wherein the (Lys,Arg) is intended to be either Lys or Arg. A preferred reagent would be $(Xaa)_{2-6}$-(Lys,Arg)-CMK. Furthermore, non-peptide affinity labels or suicide substrates that inactivate a serine protease active site could also be useful in localizing to the enzyme active site (1) a detectable label or therapeutic moiety; or (2) a chelate that contains, or a chelator that has the potential to contain, a detectable label or therapeutic moiety. These non-peptide reagents are not limited to those that modify the catalytic triad His residue, as compounds are known which can alkylate the active site Ser (e.g., diisopropyl fluorophosphate, DFP; and phenylmethylsulfonyl fluoride, PMSF). Moreover, Porter, N. A et al., *J. Am Chem Soc.* 121:7716–7717 (1999), incorporated by reference in its entirety, describes the use of photolabile moieties to modify proteases with a photoremovable "cage." Of particular utility herein is the description of 4-aminocinnamate esters to label the endosite of proteases. The present invention includes such types of modifying groups as well.

A reagent containing a chelating group must be capable of modifying a thiol or amine group. In the case of an amine-reactive reagent, because the N-terminal amine has a $pK_a$ of about 7.5 whereas the epsilon amino group of Lys has a $pK_a$ of about 9.5, these two types of amino group will have quite different reactivities within the pH range 7.5–9.5. Thus, by varying the pH of the reaction conditions, a reagent delivering the chelating group can be introduced at the N-terminus of a peptidic suicide substrate in a selective manner. The chelating group for an imageable label may be part of the reagent, for example, (Chelator)-$(Xaa)_{2-6}$-(Lys, Arg)-CMK. It is also possible to introduce a free thiol at the N-terminus of a peptidic suicide inhibitor by introducing a Cys or HomoCys residue as one of the Xaa amino acids or by chemically modifying the N-terminus of the peptide suicide substrate. The chelator may then be part of the reagent, as described above, or it may be introduced into the $(Xaa)_{2-6}$-(Lys,Arg)-CMK moiety after this peptide reagent has bound to the uPA active site. A more generic characterization of this preferred type of endosite-specific reagent is (Chelator)-$(Xaa)_{2-6}$-(Lys,Arg)-(alkylating group).

Once a particular endosite-specific reagent has bound to uPA, a new molecular entity is created which is also intended to be within the scope of this invention. This molecular entity is uPA (or other serine protease), tcuPA, or a fragment thereof that retains the endosite and the uPAR-binding epitope, to which is covalently bonded one of the above reagents. The reagent may incorporate a detectable label, a therapeutic moiety, an "empty" chelator not carrying an imageable label or therapeutic moiety (but capable of accepting one), or a chelator that does carry an imageable label or therapeutic moiety. Alternatively, the chelator, label, etc., is not necessarily incorporated into the reagent a priori; rather, the reagent would be derivatized subsequently to carry the label or moiety. The structures may be characterized as follows (where "label" means detectable label):

(Label)-(Xaa)$_{2-6}$-(Lys,Arg)-(alkylating group)-uPA;

(Therapeutic moiety)-(Xaa)$_{2-6}$-(Lys,Arg)-(alkylating group)-uPA;

(Chelator$_{(empty)}$)-(Xaa)$_{2-6}$-(Lys,Arg)-(alkylating group)-uPA; or (Label-Chelator)-(Xaa)$_{2-6}$-(Lys,Arg)-(alkylating group)-uPA.

Serine protease active sites can be fairly restrictive and may only accommodate a few amino acid residues or substrates of limited size (Nozawa et al., *J. Biochem* (1982) 91:1837–1843). The endosite-specific peptide described above does not have a per se limitation on its length (although, as indicated, peptides of 3–7 residues are preferred). This absence of a length limitation is because endosite interactions are but one possible way of localizing an alkylating moiety such as CMK to the uPA active site. Thus, another embodiment is a peptide that binds to the uPA endosite and one or more exosites. An example is an endosite-binding tripeptide which further comprises an additional peptide "tail" that binds to a surface exosite of the protein. A well-known example of such a construct is hirulog, a thrombin inhibitor. Hirulog combines the active site specificity of a thrombin-specific tripeptide and includes more peptide chain that binds to the surface of thrombin, yielding a high-affinity inhibitor of thrombin activity (Skordalakes et al. *Biochemistry* 13:14420–7).

Using similar notation to that above, a range of preferred embodiments include:

(Label)-(Peptide Z)-(Xaa)$_{2-6}$-(Lys,Arg)-(alkylating group);

(Therapeutic Moiety)-(Peptide Z)-(Xaa)$_{2-6}$-(Lys,Arg)-(alkylating group), (Chelator$_{(empty)}$)-(Peptide Z)-(Xaa)$_{2-6}$-(Lys,Arg)-(alkylating group); and (Label-Chelator)-(Peptide Z)-(Xaa)$_{2-6}$-(Lys,Arg)-(alkylating group)

wherein Peptide Z is any peptide that binds to a surface exosite of uPA.

This would give rise to at least four novel types of molecules shown below, the latter two of which are most preferred:

In yet another embodiment, a longer peptide (of between about 4 and 30 residues) that mimics the recognition region of PAI-1 is also useful as a site-specific reagent to produce a uPAR-directed imaging protein/peptide as described above.

As has been discussed earlier, other useful reagents modify uPA randomly (not necessarily being localized to the active site) to create uPAR-imaging agents.

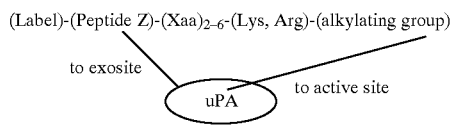

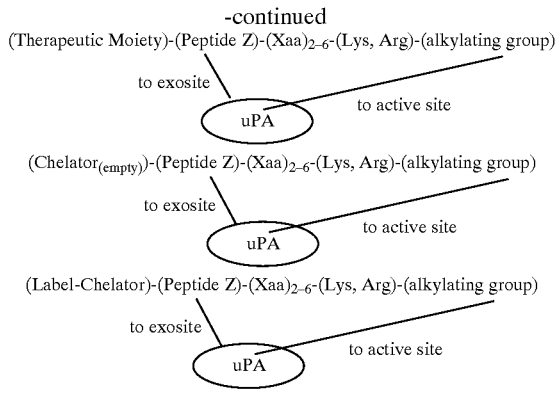

Non-Peptidic Endosite Localizing Moieties

In addition to the peptidic reagents described above, a general class of non-peptidic agents may be used to localize a chelator (and thereby, a detectable label) to the active site of uPA or of any serine protease. Such structures include, DFP and PMSF, etc. A member of this group of compounds should have the following properties:

(1) it selectively modifies only endosite residues (either the Ser or the His)

(2) it localizes a chelator or chelate only to the endosite of uPA (or other serine protease)

These reagents are selective for the active site by virtue of the fact that they are enzyme activated irreversible inhibitors and will only form covalent adducts when catalyzed by the target enzyme.

Diagnostic Methods

The methods of this invention may be used to image tumor foci in a subject. A vertebrate subject, preferably a mammal, more preferably a human, is administered an amount of the compound effective to image a tumor focus. The compound or pharmaceutically acceptable salt thereof is preferably administered in the form of a diagnostic composition as described above.

Useful doses of the compounds are defined as effective amount of the peptide for the particular diagnostic measurement. Thus, an effective amount means an amount sufficient to be detected using the appropriate detection system e.g., MRI detector, gamma camera, etc. The minimum detectable amount will depend on the ratio of labeled peptide specifically bound to a tumor (signal) to the amount of labeled peptide either bound non-specifically or found free in plasma or in extracellular fluid. The advantage of the peptides of this invention is that they are cleared rapidly from the plasma and do not accumulate in most tissues, in contrast to antibody-based contrast agents. Thus, the signal-to-noise ratio is increased and only the specifically tumor-bound peptide is detected or quantitated. This allows for accurate localization of the signal and the detection of small tumor lesions which can only be detected in the absence of high background signals.

The amount of the diagnostic composition to be administered depends on the precise peptide selected, the disease or condition, the route of administration, and the judgment of the skilled imaging professional.

A preferred dose for imaging by MRI, SPECT, etc., is an amount of up to about 100 milligrams of labeled peptide compound per kilogram of body weight. A typical single dosage of the labeled peptide is between about 1 ng and about 100 mg/kg body weight.

An alternative diagnostic approach utilizes cDNA probes that are complementary to and thereby detect uPA- and uPAR-expressing cells by in situ hybridization with mRNA in these cells. The present invention provides methods for localizing uPAR or uPA mRNA in cells using fluorescent in situ hybridization (FISH) with labeled cDNA probes that correspond to part or all of the uPA (or uPAR) coding sequence. The basic principle of FISH is that DNA or RNA in the prepared specimens are hybridized with the probe nucleic acid of this invention that is labeled non-isotopically with, for example, a fluorescent dye, biotin or digoxigenin. The hybridized signals are then detected by fluorimetric or by enzymatic methods, for example, by using a fluorescence or light microscope. The detected signal and image can be recorded on light sensitive film.

An advantage of using a fluorescent probe is that the hybridized image can be readily analyzed using a powerful confocal microscope or an appropriate image analysis system with a charge-coupled device (CCD) camera. As compared with radioactive methods, FISH offers increased sensitivity. In additional to offering positional information, FISH allows better observation of cell or tissue morphology. Because of the nonradioactive approach, FISH has become widely used for localization of specific DNA or mRNA in a specific cell or tissue type.

The in situ hybridization methods and the preparations useful herein are describe in Wu, W. et al., eds., *Methods in Gene Biotechnology*, CRC Press, 1997, chapter 13, pages 279–289. This book is incorporated by reference in its entirety, as are the references cited therein. A number of U.S. patents and scientific articles that describe various in situ hybridization techniques and applications, also incorporated by reference, are: U.S. Pat. Nos. 5,912,165; 5,906,919; 5,885,531; 5,880,473; 5,871,932; 5,856,097; 5,837,443; 5,817,462; 5,784,162; 5,783,387; 5,750,340; 5,759,781; 5,707,797; 5,677,130; 5,665,540; 5,571,673; 5,565,322; 5,545,524; 5,538,869; and 5,501,954, 5,225,326, 4,888,278. Other related references include Jowett, T, *Methods Cell Biol;* 59:63–85 (1999) Pinkel et al., *Cold Spring Harbor Symp. Quant. Biol. LI:* 151–157 (1986); Pinkel, D. et al., *Proc. Natl. Acad. Sci. (USA)* 83:2934–2938 (1986); Gibson et al., *Nucl. Acids Res.* 15:6455–6467 (1987); Urdea et al., *Nucl. Acids Res.* 16:4937–4956 (1988); Cook et al., *Nucl. Acids Res.* 16:4077–4095 (1988); Telser et al., *J. Am. Chem. Soc.* 111:6966–6976 (1989); Allen et al., *Biochemistry* 28:4601–4607 (1989); Nederlof, P. M. et al., *Cytometry* 10:20–27 (1989); Nederlof, P. M. et al., *Cytometry* 11:126–131 (1990); Seibl, R., et al., *Biol. Chem. Hoppe-Seyler* 371:939–951 (October 1990); Wiegant, J. et al., *Nucl. Acids Res.* 19:3237–3241(1991); McNeil J A et al., *Genet Anal Tech Appl* 8:41–58 (1991); Komminoth et al., *Diagnostic Molecular Biology* 1:85–87 (1992); Dauwerse, J. G. et al., *Hum. Mol. Genet.* 1:593–598 (1992); Ried, T. et al., *Proc. Natl. Acad. Sci. (USA)* 89:1388–1392 (1992); Wiegant, J. et al., *Cytogenet. Cell Genet.* 63:73–76 (1993); Glaser, V., *Genetic. Eng. News.* 16:1, 26 (1996); Speicher, M. R., *Nature Genet.* 12:368–375 (1996).

Pharmaceutical and Therapeutic Compositions and Their Administration

The compounds that may be employed in the pharmaceutical compositions of the invention include all of those compounds described above, as well as the pharmaceutically acceptable salts of these compounds. As stated above, the compounds of the invention possess the ability to inhibit invasiveness or angiogenesis, properties that are exploited in the treatment of cancer, in particular metastatic cancer. A composition of this invention may be active per se, or may act as a "pro-drug" that is converted in vivo to the active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. The pharmaceutical compositions can therefore be used to treat domestic and commercial animals, including birds and more preferably mammals, as well as humans.

Though the preferred routes of administration are systemic the pharmaceutical composition may be administered topically or transdermally, e.g., as an ointment, cream or gel; orally; rectally; e.g., as a suppository, parenterally, by injection or continuously by infusion; intravaginally; intrapenilely; intranasally; intrabronchially; intracranially, intraaurally; or intraocularly.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an affected area, e.g., skin surface, mucous membrane, eyes, etc. This amount will generally range from about 0.001 mg to about 1 g per application, depending upon the area to be treated, the severity of the symptoms, and the nature of the topical vehicle employed.

Therapeutic compositions of the invention may comprise, in addition to the labeled peptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerase inhibitors such as etoposide; or biological response modifiers, e.g., interferons or interleukins. In fact, pharmaceutical compositions comprising any known cancer therapeutic in combination with the labeled peptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

Therapeutic Compositions

In a preferred embodiment, the peptides describe herein are "therapeutically conjugated" or "therapeutically labeled" (terms which are intended to be interchangeable) and used to deliver a therapeutic agent to the site to which the compounds home and bind, such as sites of tumor metastasis or foci of infection/inflammation, restenosis or fibrosis. The term "therapeutically conjugated" means that the modified peptide is conjugated to another therapeutic agent that is directed either to the underlying cause or to a "component" of tumor invasion, angiogenesis, inflammation or other pathology.

Examples of useful therapeutic radioisotopes (ordered by atomic number) include $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb and $^{217}$Bi. These atoms can be conjugated to the peptide directly, indirectly as part of a chelate, or, in the case of iodine, indirectly as part of an iodinated Bolton-Hunter group.

Preferred doses of the radionuclide conjugates are a function of the specific radioactivity to be delivered to the target site which varies with tumor type, tumor location and vascularization, kinetics and biodistribution of the peptide carrier, energy of radioactive emission by the nuclide, etc. Those skilled in the art of radiotherapy can readily adjust the dose of the labeled peptide in conjunction with the dose of the particular nuclide to effect the desired therapeutic benefit without undue experimentation.

Another therapeutic approach included here is the use of boron neutron capture therapy (NCT), where a boronated peptide is delivered to a desired target site, such as a tumor, most preferably an intracranial tumor (Barth, R. F., *Cancer Invest.* 14:534–550 (1996); Mishima, Y. (ed.), *Cancer Neutron Capture Therapy*, New York: Plenum Publishing Corp., 1996; Soloway, A. H., et al., (eds), *J. Neuro-Oncol.* 33:1–188 (1997). The stable isotope $^{10}$B is irradiated with low energy (<0.025 eV) thermal neutrons, and the resulting nuclear capture yields α particles and $^{7}$Li nuclei which have high linear energy transfer and respective path lengths of about 9 and 5 $\mu$m. This method is predicated on $^{10}$B accumulation in the tumor with lower levels in blood, endothelial cells and normal tissue (e.g., brain). Such delivery has been accomplished using epidermal growth factor (Yang. W. et al., *Cancer Res* 57:4333–4339 (1997). Because of the selective expression of uPAR in tumors, the peptides of the present invention are excellent delivery vehicles for this therapeutic moiety.

In addition to boron NCT, gadolinium, specifically $^{157}$Gd appears to be particularly advantageous for use in NCT with the present peptides. It has recently been reported (Tokumitsu, H. et al., *Chem Pharm Bull* 47:838–842 (1999), incorporated by reference in its entirety) that: $^{157}$Gd has the highest thermal neutron capture cross section (255,000 barns) among naturally occurring isotopes, 66 times larger than that of $^{10}$B; Gd neutron capture reaction releases the long range (>100 $\mu$m) prompt γ-rays, internal conversion electrons, X-rays and Auger electrons. Thus, Gd-NCT may increase the chance for photons to hit tumor cells and for electrons to damage these cell locally and intensively. Another advantage is that Gd has long been used as a MRI imaging diagnostic agent. It will be possible to integrate Gd-NCT with MRI diagnosis by using the Gd-loaded dosage forms of the present peptides. A preferred form of Gd for labeling the peptides of this invention for use in Gd-NCT is gadopentetic acid (Gd-DTPA).

Other therapeutic agents which can be coupled to the peptide compounds according to the method of the invention are drugs, prodrugs, enzymes for activating pro-drugs, photo-sensitizing agents, gene therapeutics, antisense vectors, viral vectors, lectins and other toxins.

The therapeutic dosage administered is an amount that is therapeutically effective, as is known to or readily ascertainable by those skilled in the art. The dose is also dependent upon the age, health, and weight of the recipient, kind of concurrent treatment(s), if any, the frequency of treatment, and the nature of the effect desired, such as, for example, anti-inflammatory effects or anti-bacterial effect.

Lectins are proteins, commonly derived from plants, that bind to carbohydrates. Among other activities, some lectins are toxic. Some of the most cytotoxic substances known are protein toxins of bacterial and plant origin (Frankel, A. E. et al., *Ann. Rev. Med.* 37:125–142 (1986)). These molecules binding the cell surface and inhibit cellular protein synthesis. The most commonly used plant toxins are ricin and abrin; the most commonly used bacterial toxins are diphtheria toxin and *Pseudomonas* exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908–5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., *FEBS Lett.* 195:1–8 (1986)). Diphtheria toxin and *Pseudomonas* exotoxin A are also single chain proteins, and their binding and toxicity functions reside in separate domains of the same protein chain with full toxin activity requiring proteolytic cleavage between the two domains. *Pseudomonas* exotoxin A has the same catalytic activity as diphtheria toxin. Ricin has been used therapeutically by binding its toxic α-chain, to targeting molecules such as antibodies to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus. Conjugation of toxins to protein such as antibodies or other ligands are known in the art (Olsnes, S. et al., *Immunol. Today* 10:291–295 (1989); Vitetta, E. S. et al., *Ann. Rev. Immunol.* 3:197–212 (1985)).

Cytotoxic drugs that interfere with critical cellular processes including DNA, RNA, and protein synthesis, have been conjugated to antibodies and subsequently used for in vivo therapy. Such drugs, including, but not limited to, daunorubicin, doxorubicin, methotrexate, and mitomycin C are also coupled to the compounds of this invention and used therapeutically in this form.

In another embodiment of the invention, photosensitizers may be coupled to the compounds of the invention for delivery directly to a tumor.

Therapeutic Methods

The methods of this invention may be used to inhibit tumor growth and invasion in a subject or to suppress angiogenesis induced by tumors by inhibiting endothelial cell growth and migration. By inhibiting the growth or invasion of a tumor or angiogenesis, the methods result in inhibition of tumor metastasis. A vertebrate subject, preferably a mammal, more preferably a human, is administered an amount of the compound effective to inhibit tumor growth, invasion or angiogenesis. The compound or pharmaceutically acceptable salt thereof is preferably administered in the form of a pharmaceutical composition as described above.

Doses of the compounds preferably include pharmaceutical dosage units comprising an effective amount of the peptide. By an effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20% of patients is considered efficacious (Frei III, E., *The Cancer Journal* 3:127–136 (1997)). However, an effect of this magnitude is not considered to be a minimal requirement for the dose to be effective in accordance with this invention.

In one embodiment, an effective dose is preferably 10-fold and more preferably 100-fold higher than the 50% effective dose ($ED_{50}$) of the compound in an in vivo assay as described herein.

The amount of active compound to be administered depends on the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 milligrams of active compound per kilogram of body weight. A typical single dosage of the peptide is between about 1 ng and about 100 mg/kg body weight. For topical administration, dosages in the range of about 0.01–20% concentration (by weight) of the compound, preferably 1–5%, are suggested. A total daily dosage in the range of about 0.1 milligrams to about 7 grams is preferred for intravenous administration. The foregoing ranges are, however, suggestive, as the number of variables in an individual treatment regime is large, and considerable excursions from these preferred values are expected.

An effective amount or dose of the peptide for inhibiting invasion in vitro is in the range of about 1 picogram to about 0.5 nanograms per cell. Effective doses and optimal dose ranges may be determined in vitro using the methods described herein.

The foregoing compositions and treatment methods are useful for inhibiting cell migration and invasion or cell proliferation in a subject having any disease or condition associated with undesired cell invasion, proliferation, angiogenesis or metastasis. Such diseases or conditions may include primary growth of solid tumors or leukemias and lymphomas, metastasis, invasion and/or growth of tumor metastases, benign hyperplasias, atherosclerosis, myocardial angiogenesis, angiofibroma, arteriovenous malformations, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions including psoriasis scleroderma, hemangioma, hemophilic joints, hypertrophic scars, Osler-Weber syndrome, psoriasis, pyrogenic granuloma, retrolental fibroplasia, scleroderma, Von-Hippel-Landau syndrome, trachoma, vascular adhesions, lung fibrosis, chemotherapy-induced fibrosis, wound healing with scarring and fibrosis, peptic ulcers, fractures, keloids, and disorders of vasculogenesis, hematopoiesis, ovulation, menstruation, pregnancy and placentation, or any other disease or condition in which invasion or angiogenesis is pathogenic or undesired.

More recently, it has become apparent that angiogenesis inhibitors may play a role in preventing inflammatory angiogenesis and gliosis following traumatic spinal cord injury, thereby promoting the reestablishment of neuronal connectivity (Wamil, A. W. et al., *Proc. Nat'l. Acad. Sci. USA* 95:13188–13193 (1998)). Therefore, the compositions of the present invention are administered as soon as possible after traumatic spinal cord injury and for several days up to about two weeks thereafter to inhibit the angiogenesis and gliosis that would sterically prevent reestablishment of neuronal connectivity. The treatment reduces the area of damage at the site of spinal cord injury and facilitates regeneration of neuronal function and thereby prevents paralysis. The compounds of the invention are expected also to protect axons from Wallerian degeneration, reverse aminobutyrate-mediated depolarization (occurring in traumatized neurons), and improve recovery of neuronal conductivity of isolated central nervous system cells and tissue in culture.

Having now generally described the invention, the same will be more readily understood through reference to the following examples which are provided by way of illustration, and are not intended to be limiting of the present invention, unless specified.

EXAMPLE I

Binding of the Peptides to HeLa Cells

The compounds of the invention are tested for their binding to uPAR by measuring their ability to inhibit the binding of [$^{125}$I]DFP-uPA (catalytically inactivated high molecular weight uPA) to uPAR expressed by HeLa (human cervical carcinoma) cells. Cells (about $5 \times 10^4$/well) are plated (in MEM with Earle's salts/10% FBS+antibiotics) in 24-well plates, then incubated in a humid 5% $CO_2$ atmosphere until the cells reach 70% confluence. Catalytically inactivated high molecular weight uPA (DFP-uPA) is radio-iodinated using Iodo-gen® (Pierce) to a specific activity of about 250,000 cpm/mg. The cell-containing plates are then chilled on ice and the cells washed twice (5 minutes each) with cold PBS/0.05% Tween-80. Test compounds are serially diluted in cold PBS/0.1% BSA/0.01% Tween-80 and added to each well to a final volume of 0.3 mL 10 minutes prior to the addition of the [$^{125}$I]DFP-uPA. Each well then receives 9500 cpm of [$^{125}$I]DFP-uPA at a final concentration of 0.2 nM. The plates are incubated at 4° C. for 2 hrs, after which time the cells are washed 3× (5 minutes each) with cold PBS/0.05% Tween-80. NaOH (1 N; 0.5 mL) is added to each well to lyse the cells, the contents of each well are aspirated and the total counts in each well determined using a gamma counter. Each compound is tested in triplicate and the results are expressed as a percentage of the total radioactivity measured in wells containing [$^{125}$I]DFP-uPA alone, which is taken to represent maximum (100%) binding.

The peptides of this invention inhibit the binding of [$^{125}$I]DFP-uPA with an IC$_{50}$ of ranging between about 0.1 nM to 2 µM. Modification of the peptides with diagnostic of therapeutic labels does not significantly affect their measured affinity constants.

EXAMPLE II

Oregon Green-Labeled-Peptide Targeting to Tumor Cells

The ability of Oregon Green-labeled-peptides to localize to tumor cells is assessed by fluorescence microscopy. Tumor cells are cultured for 24 hours on coverslips (in a 6-well plate). Oregon Green-labeled peptides (1 µM) are added to each well and allowed to incubate in the presence of the cells. The coverslips are removed from the wells and washed twice (5 minutes per wash) with PBS in a second 6-well plate. The coverslips are mounted onto slides and the fluorescence observed using a fluorescent microscope. Digitized images are captured using a video camera and NIH image.

Binding of Oregon Green-labeled-peptides is observed on tumor cells but is generally absent or very weak on normal cells.

EXAMPLE III

Imaging of Tumors In Vivo by uPAR-Targeting Ligand

MDA-MB-231 human breast cancer cells (1×10$^6$) are inoculated s.c. into the flank of female Balb/c (nu/nu) mice. Tumors are allowed to grow for varying lengths of time. Labeled uPAR targeting peptides (50 µg/injection) are injected i.p. and the ability of these peptides to localize to and detect the tumors is assessed at various times post-injection using the appropriate imaging technique.

EXAMPLE IV

Detection of Experimental Metastasis of Tumor Cells In Vivo by uPA Peptides The peptides described above are also tested in vivo in a model of human tumor metastasis in nude mice. PC-3 cells are inoculated into nude mice i.v. at doses of 1×10$^6$ cells per mouse. These mice are administered the imaging agent as above. The localization of the labeled peptide is imaged using the appropriate detection technique.

In one study, PC-3 cells are transfected with the gene encoding the enzyme chloramphenicol acetyl-transferase (CAT). At termination of the study, the animals are euthanized and the tumor marker probe CAT is assayed in regional lymph nodes, femurs, lungs, and brain. The localization of the labeled peptide is compared to the actual presence and amount of tumor in a given tissue or site.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A UPA active site-targeting peptide compound that binds to the endosite and one or more exosites of (i) tcupA or (ii) a fragment or subunit of tcupA, which fragment or subunit retains the UPA (1) enzymatic endosite and (2) a uPAR-binding epitope, such that said peptide compound covalently modifies the endosite; said peptide compound being a member of the group consisting of:
 (a) (Chelator)-(Xaa)$_{2-6}$-(Lys,Arg)-(alkylating group)-uPA;
 (b) (Label-Chelator)-(Xaa)$_{2-6}$-(Lys,Arg)-(alkylating group)-uPA;
 (c) (Labels (Xaa)$_{2-6}$-(Lys,Arg)-(alkylating group)-uPA; and
 (d) (Therapeutic moiety)-(Xaa)$_{2-6}$-(Lys,Arg)-(alkylating group)-uPA;
 wherein Label is a detectable label, each Xaa is independently an amino acid; and wherein the peptide compound localizes said chelator, detectable label or therapeutic moiety to the uPA active site.

2. A method for detecting the presence of uPAR (i) on the surface of a cell, (ii) in a tissue, (iii) in an organ or (iv) in a biological sample, which cell, tissue, organ or sample is suspected of expressing uPAR comprising the steps of:
 (a) contacting the cell, tissue, organ or sample with the peptide compound of (Label-Chelator)-(Xaa)$_{2-6}$-(Lys,Arg)-(alkylating group)-uPA or (Label)-(Xaa)$_{2-6}$-(Lys,Arg)-(alkylating group)-uPA from claim 1; and (b) detecting the presence of the label associated with the cell, tissue, organ, or sample.

3. The method of claim 2 wherein the contacting and the detecting are in vitro.

4. The method of claim 2 wherein the contacting is in vivo and the detecting is in vitro.

5. The method of claim 2 wherein the contacting and the detecting are in vivo.

6. A diagnostic or therapeutic uPA active site-targeting peptide pharmaceutical composition comprising:
 (a) an effective amount of the peptide of claim 1; and
 (b) a pharmaceutically acceptable carrier.

7. The pharmaceutical composition of claim 6 in a form suitable for injection.

8. The therapeutic pharmaceutical composition of claim 6 wherein the therapeutically active moiety is a radionuclide.

9. The therapeutic pharmaceutical composition of claim 8, wherein the radionuclide is selected from the group consisting of $^{47}$Sc, $^{67}$Cu, $^{90}$Y, $^{109}$Pd, $^{125}$I, $^{131}$I, $^{186}$Re, $^{188}$Re, $^{199}$AU, $^{211}$At, $^{212}$Pb and $^{217}$Bi.

10. A method for inhibiting cell migration, cell invasion, cell proliferation or angiogenesis, or for inducing apoptosis, comprising contacting cells with an effective amount of a therapeutic pharmaceutical composition according to claim 6.

11. A method for inhibiting the invasiveness of tumor cells comprising contacting the cells with an effective amount of a therapeutic pharmaceutical composition according to claim 6.

12. The compound of claim 1, which is:

(Chelator)-(Xaa)$_{2-6}$-(Lys,Arg)-(alkylating group)-uPA, wherein each Xaa is independently and amino acid.

13. The compound of claim 1, which is: (Label-Chelator)-(Xaa)$_{2-6}$-(Lys,Arg)-(alkylating group)-uPA where Label is a detectable label and each Xaa is independently an amino acid.

14. The compound of claim 1, which is:

(Label)-(Xaa)$_{2-6}$-(Lys,Arg)-(alkylating group)-uPA, wherein Label is a detectable label and each Xaa is an amino acid.

15. The compound of claim 1, which is:

(Therapeutic moiety)-(Xaa)$_{2-6}$-(Lys,Arg)-(alkylating group)-uPA, wherein each Xaa is independently an amino acid.

16. A diagnostic or therapeutic uPA active site-targeting pharmaceutical composition, comprising an effective amount of the peptide of claim 12 and a pharmaceutically acceptable carrier.

17. A diagnostic or therapeutic uPA active site-targeting pharmaceutical composition, comprising an effective amount of the peptide of claim 13 and a pharmaceutically acceptable carrier.

18. A diagnostic or therapeutic uPA active site-targeting pharmaceutical composition, comprising an effective amount of the peptide of claim 14 and a pharmaceutically acceptable carrier.

19. A diagnostic or therapeutic uPA active site-targeting pharmaceutical composition, comprising an effective amount of the peptide of claim 15 and a pharmaceutically acceptable carrier.

* * * * *

SEQUENCE LISTING

<160> NUMBER OF SEQ ID NOS: 2

<210> SEQ ID NO 1
<211> LENGTH: 44
<212> TYPE: PRT
<213> ORGANISM: Homo sapiens

<400> SEQUENCE: 1

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile
        35                  40

<210> SEQ ID NO 2
<211> LENGTH: 7
<212> TYPE: PRT
<213> ORGANISM: Artificial Sequence
<220> FEATURE:
<221> NAME/KEY: misc_feature

```
-continued

<222> LOCATION: ()..()
<223> OTHER INFORMATION: uPA active site-targeting compound
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (1)..(2)
<223> OTHER INFORMATION: Xaa at positions 1 and 2 must be present
<220> FEATURE:
<221> NAME/KEY: misc_feature
<222> LOCATION: (3)..(6)
<223> OTHER INFORMATION: Xaa at positions 3 to 6 may be present
<220> FEATURE:
<221> NAME/KEY: misc_feature
<222> LOCATION: (7)..(7)
<223> OTHER INFORMATION: Xaa can be Lys or Arg

<400> SEQUENCE: 2

Xaa Xaa Xaa Xaa Xaa Xaa Xaa
1               5
```